United States Patent [19]

Lerner

[11] Patent Number: 5,562,098
[45] Date of Patent: Oct. 8, 1996

[54] ULTRASONIC MEASUREMENT OF BLOOD FLOW VELOCITY INDEPENDENT OF PROBE ANGLE

[75] Inventor: David A. Lerner, Metuchen, N.J.

[73] Assignee: LifeSigns Corporation, Minneapolis, Minn.

[21] Appl. No.: 406,713

[22] Filed: Mar. 20, 1995

[51] Int. Cl.$^6$ ........................................ A61B 8/00
[52] U.S. Cl. ........................................ 128/662.01
[58] Field of Search ............. 128/660.05, 661.08, 128/661.09, 661.1, 662.01; 73/861.25, 861.27, 861.28, 861.29, 861.31

[56] References Cited

U.S. PATENT DOCUMENTS

| | | | |
|---|---|---|---|
| 3,525,976 | 8/1970 | Wilcox et al. | 346/1 |
| 3,889,533 | 6/1975 | Balser | 73/189 |
| 3,987,673 | 10/1976 | Hansen | 73/194 |
| 4,265,126 | 5/1981 | Papadofrangakis et al. | 73/861 |
| 4,370,985 | 2/1983 | Takeichi et al. | 128/663 |
| 4,651,742 | 3/1987 | Namekawa et al. | 128/663 |
| 4,719,923 | 1/1988 | Hartwell et al. | 128/663 |
| 4,800,891 | 1/1989 | Kim | 128/661 |
| 4,924,869 | 5/1990 | Takeuchi et al. | 128/660 |
| 5,441,052 | 8/1995 | Miyajima | 128/661.09 |
| 5,443,071 | 8/1995 | Banjanin et al. | 128/661.09 |

*Primary Examiner*—George Manuel
*Attorney, Agent, or Firm*—Schwegman, Lundberg, Woessner & Kluth, P.A.

[57] ABSTRACT

An ultrasonic blood flow velocimeter for measuring the velocity of blood flowing in an artery or vein beneath the skin of a patient, by insonating the tissue with ultrasonic energy, receiving doppler-shifted signals reflected by the blood and processing the signals to determine blood velocity. The signal processing and calculations result in an accurate measure of velocity which is independent of the angle between the probe and the blood flow. This gives more accurate results than other ultrasonic methods which approximate results because of angle dependency and the fact that in general this angle is unknown. The invention can also detect and discriminate between forward and reverse flows, even when they occur simultaneously, as in the case of insonating an artery and vein with opposite flows. The invention can also measure peak flow velocity, though efficient time domain processing of signals.

19 Claims, 7 Drawing Sheets

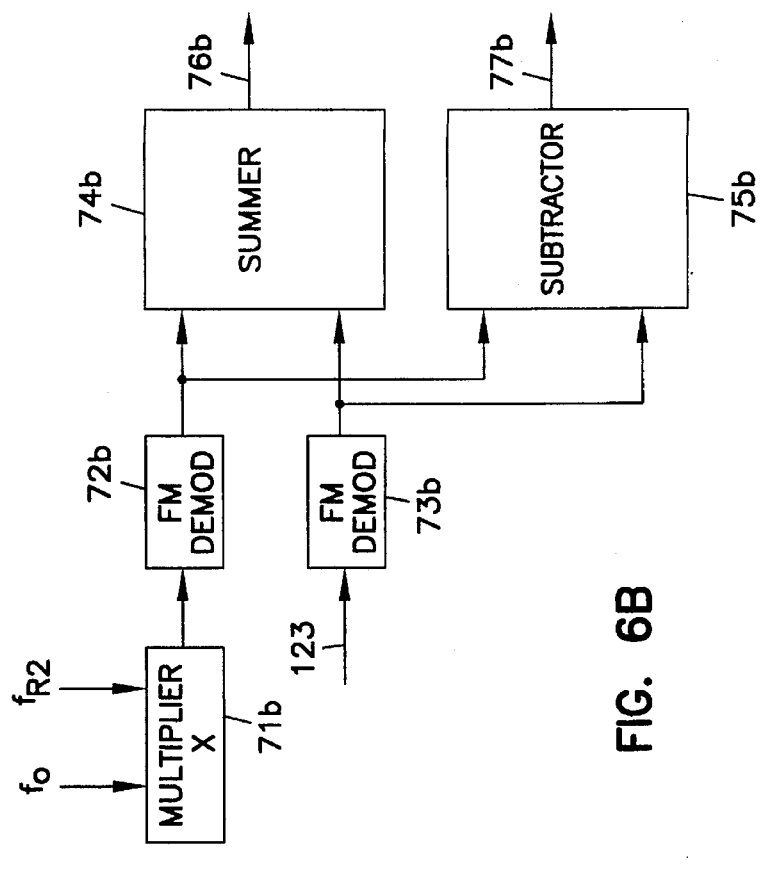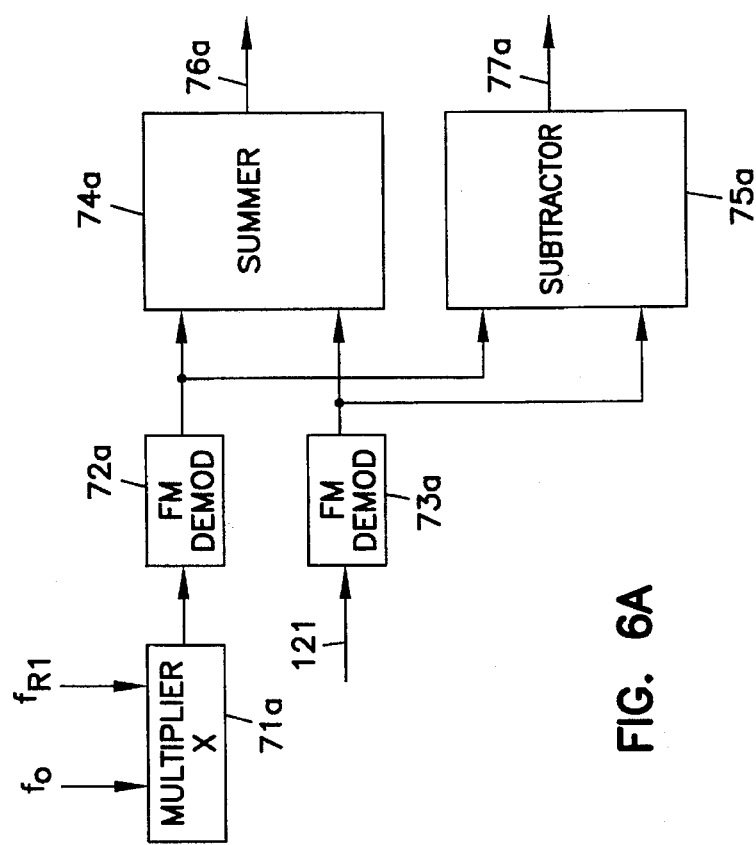
FIG. 6B
FIG. 6A

ULTRASONIC MEASUREMENT OF BLOOD FLOW VELOCITY INDEPENDENT OF PROBE ANGLE

FIELD OF THE INVENTION

This invention relates to the field of non-invasive ultrasonic devices and methods for measuring the velocity of blood flow in blood vessel through the insonation of an area containing the blood flow with ultrasonic energy, and analyzing the doppler-shifted reflections therefrom to derive velocity information.

More specifically, this invention pertains to an improved ultrasonic hemodynamic velocimeter whose performance and accuracy are not dependent upon a predetermined or separately measured angular relationship between the ultrasonic probe and the blood flow in the artery or vein to be measured.

BACKGROUND OF THE PRIOR ART

There are many situations in clinical and research medicine wherein it is desired to measure the blood flow velocity within a particular artery or vein within a body. While a number of invasive techniques have been developed to make precise measurements, in many cases such techniques are undesirable or impractical, and non-invasive methods are preferred. Most of these methods involve transmitting ultrasonic energy into an area of tissue containing the blood flow to be measured, and receiving energy reflected from that area. Energy reflected from targets such as the red blood cells which are moving will be shifted in frequency according to the well-known doppler effect. By measuring the doppler shift, these methods provide a measure of the blood flow velocity.

In practice, however, there are a number of factors which interfere with the accuracy of measurements made by these techniques. The pattern of insonating energy may be large compared to the dimensions of the vessel to be measured, and the reflected signal may contain reflections from other vessels or body structures leading to difficulties in discriminating the connect signals. It could simultaneously cover an artery and vein with blood flows in opposite directions. The location of the blood vessel may not be precisely known in relationship to the probe placement. More significantly, the angle between the direction of the transmitted ultrasonic energy and the direction of blood flow has caused many difficulties. Since in general it is not possible to have the ultrasonic beam co-axial with the blood flow, a cosine error is introduced. To correct for this cosine error, it has been necessary in the prior art to try to measure the actual angle, or to assume it lies within a certain range and approximate accordingly, with acceptance of a loss in accuracy.

To overcome these problems, the prior art has proposed a variety of systems. In some systems which provide an ultrasonic image as well as a doppler shift measurement of velocity, attempts have been made to graphically measure the orientation angle of the probe and vessel and use it in a correction formula. However, such measurements are imprecise, leading to corresponding imprecision in the calculated value. Other systems have employed arrays of transmitters or receivers, and a wide variety of signal processing approximations and assumptions to correct for the angular orientation of the probe with respect to the blood vessel.

These prior art techniques, while providing some improvements, are still subject to certain inaccuracies. In some cases, there are angle limitations on the placement of the probe, such that they will only work if a known small range of angles is maintained. Such systems may exhibit repeatability errors. Other systems rely on precise carrier rejection and notch filters, but these components are expensive to implement in the ultrasonic frequency range, and typically exhibit drift due to temperature and ageing. Other systems use signal processing which depends greatly on receiver sensitivity and cross-symmetry, which also makes them expensive to make, and difficult to maintain in calibration.

SUMMARY OF THE INVENTION

To overcome these and other problems in the prior art, the present invention provides an improved velocimeter which is fully independent of the probe angle. The invention can also detect forward and reverse flows, even when they occur simultaneously, as in the case of insonating an artery and vein with opposite flows. The invention can also measure peak flow velocity, though efficient time domain processing of signals. These and other features and advantages of the invention will become apparent from the following description of the preferred embodiment of the invention.

BRIEF DESCRIPTION OF THE DRAWING

In the drawing.

FIGS. 6A and 6B are block diagram in greater detail of the channel separator element of the system as shown in FIG. 4.

DESCRIPTION OF THE PREFERRED EMBODIMENT

Figure 1:
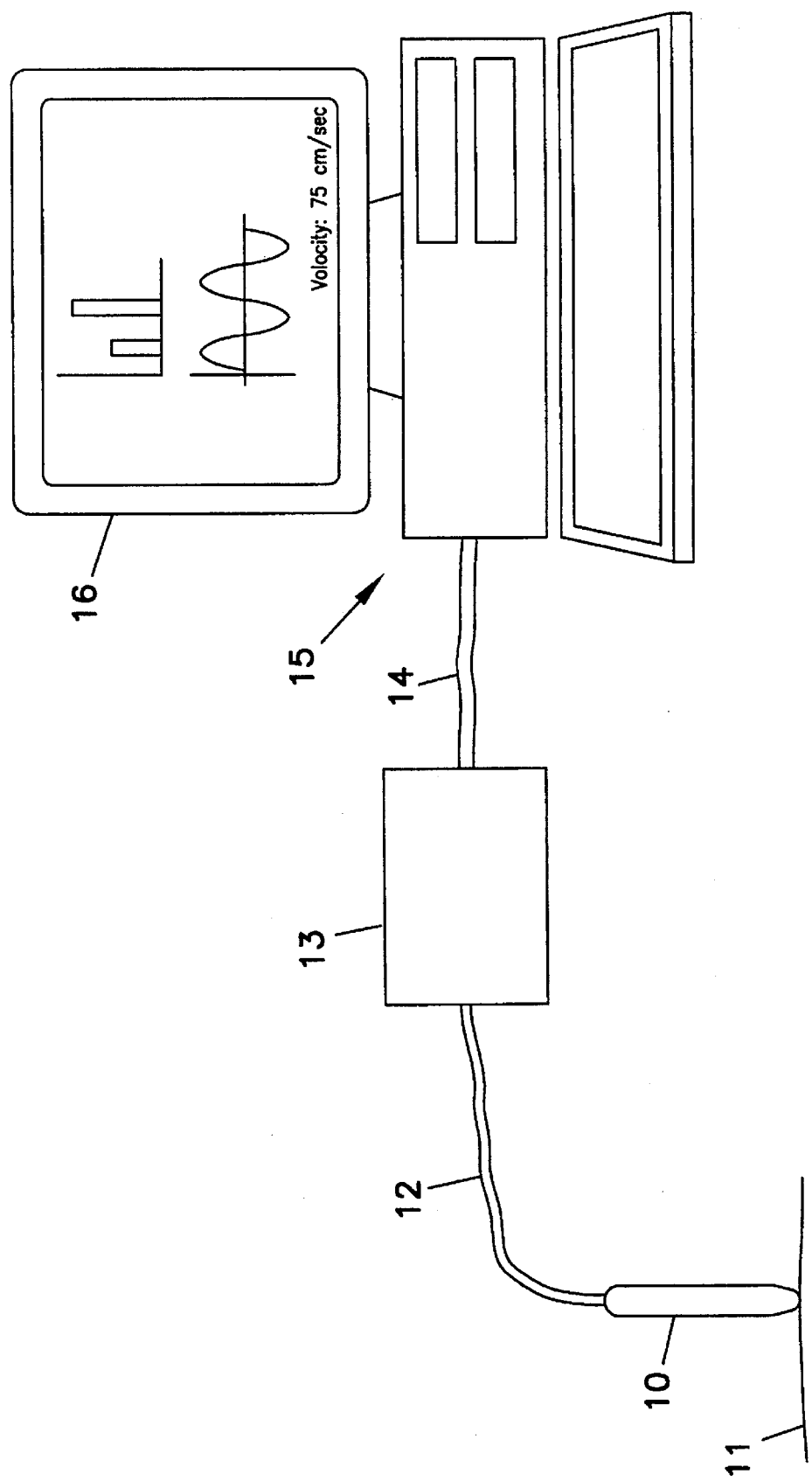
FIG. 1 is a diagrammatic view of a velocimeter according to the present invention, illustrating a probe, electronic processor, computer and display.
Figure 2A:
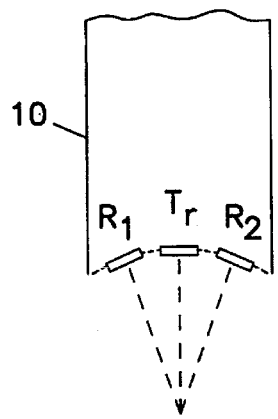
FIG. 2A is a diagrammatic view of a section of the probe end, illustrating the preferred placement of the ultrasonic transmitter and receivers.
Figure 2B:
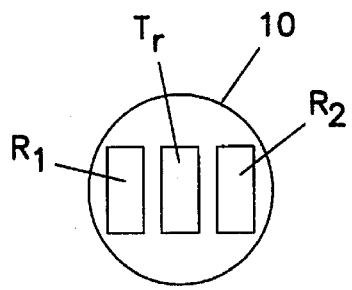
FIG. 2B is an end view of the probe of FIG. 2A.

With reference to FIG. 1, the overall operating configuration and environment of the invention is shown. It includes an ultrasonic probe 10 shown in contact with a patient's skin 11 for measurement of the flow velocity of blood in a vessel therein. Probe 10 connects to signal processor 13, an output of which connects via cable 14 to a computer system 15. This includes a CRT display 16 which shows various displays of data, as explained below.

Figure 3:
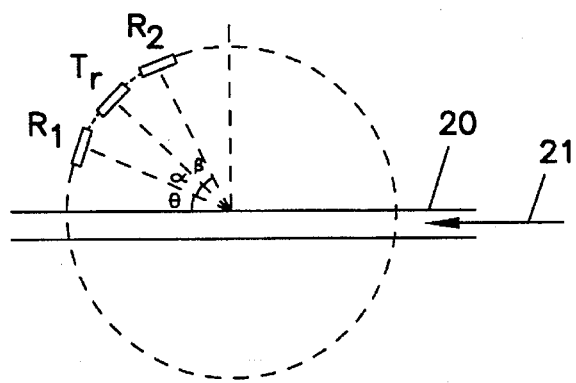
FIG. 3 is a diagram illustrating the geometric relationships of transmitter, receivers and blood flow.

The probe 10 includes three ultrasonic transducers, in the form of piezoelectric elements, as is generally known in the art, designated by reference symbols Tr, R1 and R2. Element Tr is centrally placed, and is used as the transmitter. Elements R1 and R2 are receivers, and are placed on either side of Tr, and are aligned so that Tr, R1 and R2 all cross at a common focus point, which defines generally the zone of measurement. Preferably R1 and R2 are spaced from Tr at the same angle; and preferably, Tr, R1 and R2 are arranged such that they are equidistant from the target focal point, as indicated in FIG. 3. These conditions are helpful in that they insure low amplitude modulation distortion symmetry, but are not necessary, because the calculations used can handle situations where the angles and the distances to the focus are not equal. In practice, equality in these factors could not be assured, anyway, because of minute variances that are likely to occur in the manufacture of the probes.

FIG. 3 illustrates the relationships of the transmitter Tr, receivers R1 and R2, and the blood flow indicated by arrow 21 within a vessel 20. For simplicity the figure shows the angles measured from the top of the vessel, but in practice as the probe is moved around and tilted, the focus can be brought to any depth within the vessel, to get the best result. The angle $\alpha$ is the angle between Tr and R1 from the focus, and $\beta$ is the angle between Tr and R2. As mentioned, these are preferably as close to equal as reasonable manufacturing techniques permit, but in general this is not a requirement, because the calculation technique used in the invention can handle unequal angles.

The probe is shown as being tilted at an angle with respect to the direction of blood flow in the vessel, and this angle in general is not known. Angle $\theta$ is the angle between R1 and the direction of flow in the vessel. In this example, the tilt of the probe is such that R1 is the receiver which is the one most parallel to the flow.

Figure 4:
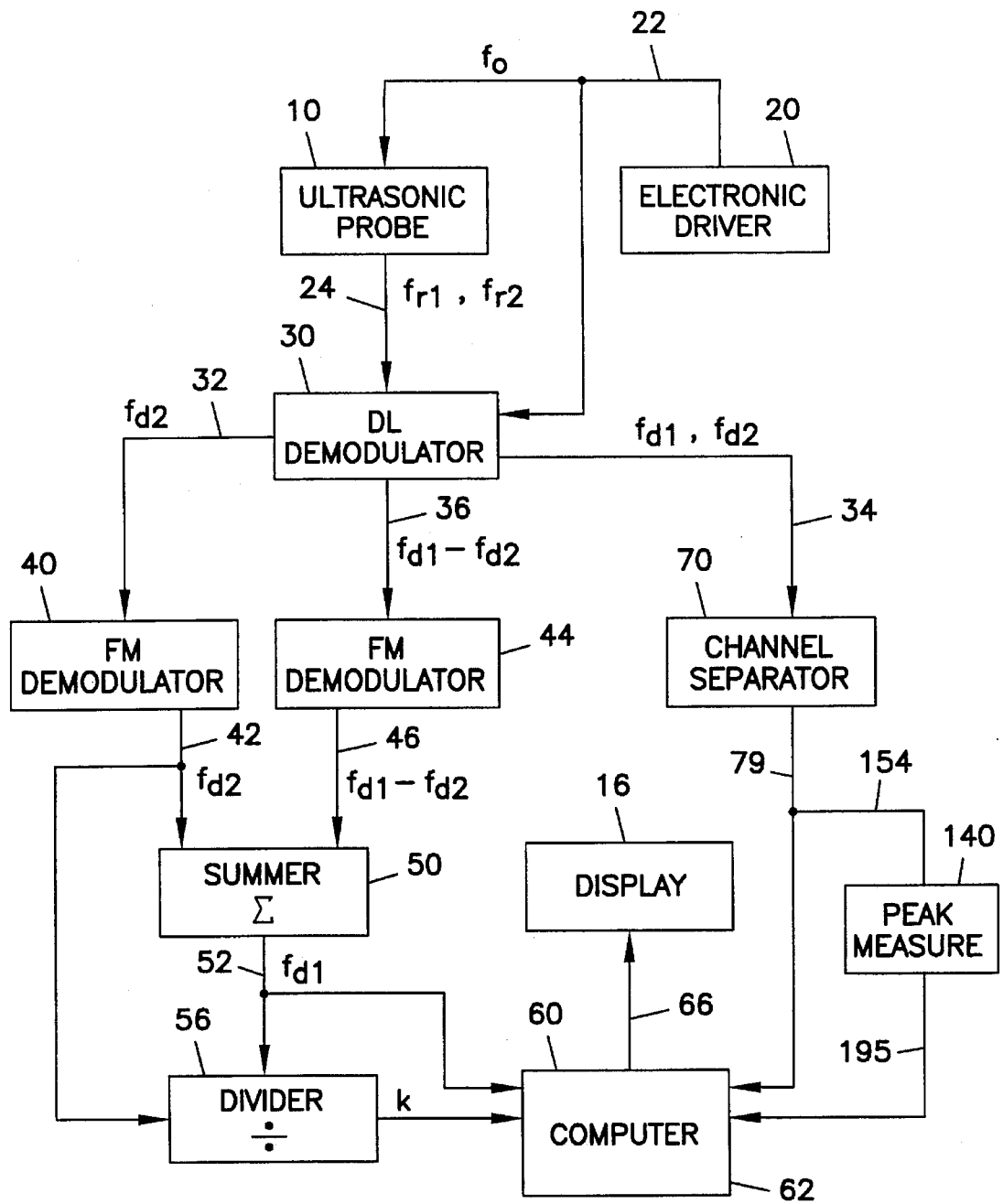
FIG. 4 is a block diagram of the overall signal processing used in the invention for the measurement of blood flow velocity.

Referring now to FIG. 4, there is shown a block diagram of the overall signal processing used in the invention for the measurement of blood flow velocity. FIG. 4 and the other Figures are schematic in nature, and represent functions or processing steps which may be implemented in a number of different ways. Most of the functions could be implemented in analog, digital or hybrid circuits, or in programmed microprocessors. The choice depends on the environment of the particular application of the invention, and speed and cost factors. For example, implementing much of the signal processing which will be described below in a programmed digital computer is possible, but will require a relatively high processing power computer, if high data rates approaching real time processing are to be attained, and this in turn will add cost to the system. Alternatively, analog circuits which can handle the ultrasonic frequencies involved are relatively inexpensive, and using them form a large part of the preliminary signal processing keeps speed up and permits the use of a lower cost, lower performance computer for the final calculations and display. For this reason, a mixed analog-digital implementation may be the best choice.

Probe 10 receives a reference, or driving signal on signal lead 22 which is applied to the transmitter element Tr (FIG. 3), and the received signals from the two receiver elements R1, R2 (FIG. 3) are provided over signal path 24 (which can consist of more that one physical lead.) Specifically, electronic driver 20 contains oscillator and driver circuitry as is generally known, to provide the ultrasonic drive frequency, referred to herein as $f_0$, for the transmitter element. The signals received by R1 and R2 are referred to herein by their frequencies $f_{r1}$ and $f_{r2}$, which in general have been doppler-shifted from $f_0$ by the motion of the blood cells.

These signals are provided to double demodulator 30, the detailed operation of which is described below with reference to FIG. 5. The overall function of this element is to provide output signals $f_{d1}$ and $f_{d2}$ on signal path 34, $f_{d2}$ on signal path 32, and the difference signal $f_{d1}-f_{d2}$ on path 36, where $f_{d1}$ and $f_{d2}$ are the difference frequencies, also called the doppler frequencies, representing the differences, for $f_1$ and $f_2$, respectively, from the reference carrier frequency $f_0$.

The signals $f_{d1}$ and $f_{d2}$ are provided to channel separator 70, which provides as outputs on path 79, the forward and reverse signals, which are described below in connection with FIGS. 6A and 6B.

A peak blood velocity subsystem 140 is provided. It is connected to receive signals from channel separator 70, and functions, as explained in detail below, to determine peak frequency and velocity.

A pair of FM demodulators 40, 44 are provided. In an analog implementation, there are many types of FM demodulators which may used, such as frequency to voltage converters, which produce an output voltage proportional to the input frequency. The signal $f_{d2}$ is input via path 32, and the difference signal $f_{d1}-f_{d2}$ is input to 44 via path 36. The demodulated signal $f_{d2}$ is provided at path 42, and the demodulated signal $f_{d1-fd2}$ is provided at path 46. These two signals are added in summer 50, and the sum, which is $f_{d1}$ is provided at path 52. Divider 56 receives $f_{d1}$ from summer 50, and $f_{d2}$ from demodulator 40, and provides their ratio, $f_{d2}/f_{d1}$ which is defined as the ratio K used in the analysis which follows.

Note that divider 56 could also be either analog or digital, and a good choice would be to use analog components up through element 56, then input into a digital computer 15 for the remaining signal processing and display of results.

Computer 15 receives the ratio K, signal $f_{d1}$, and $f_r$ or $f_f$ from channel separator 70. After conversion to digital signals, they are processed according to the invention as described below to obtain and display blood velocity on monitor 16.

Figure 5:
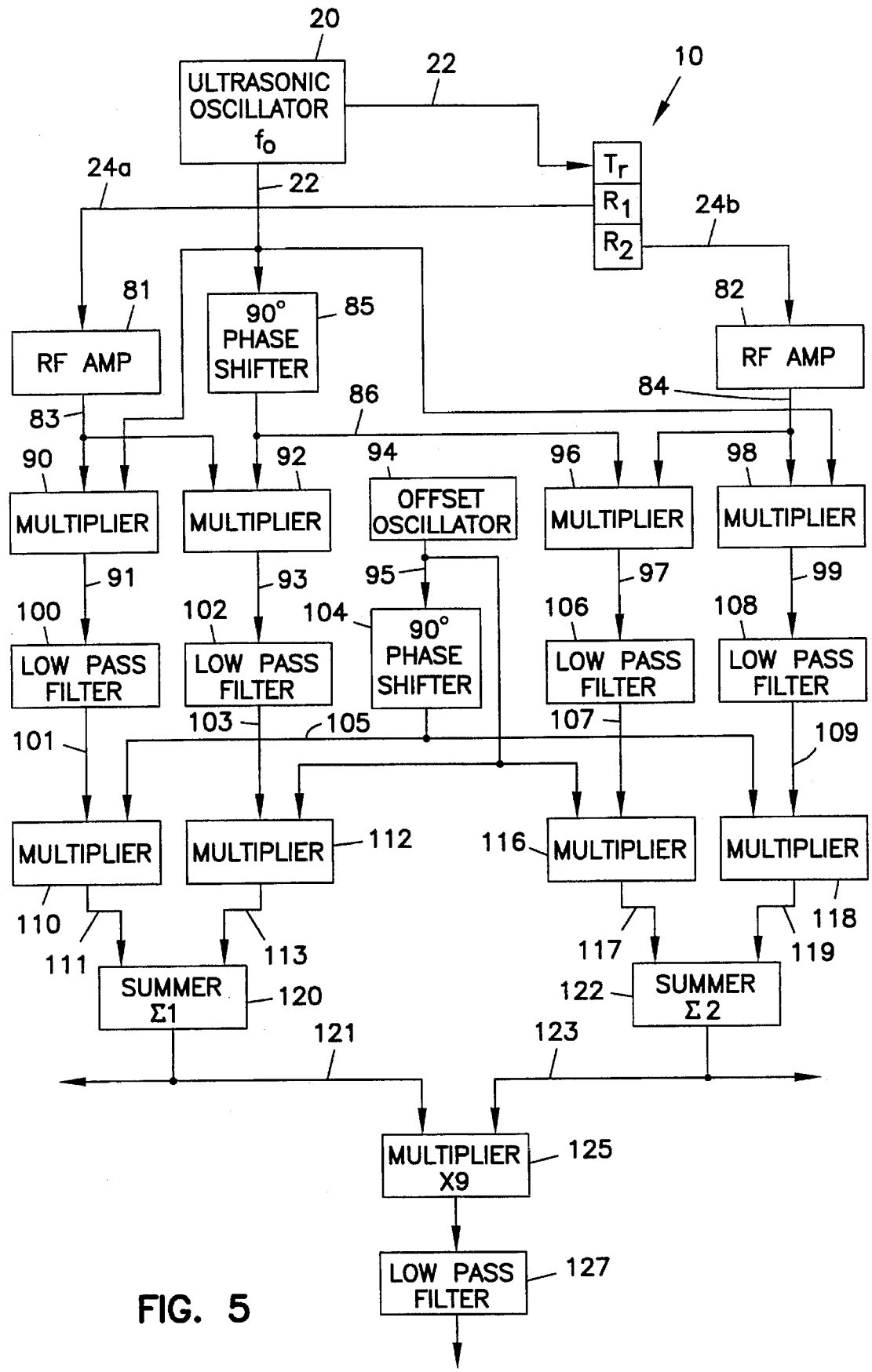
FIG. 5 is a block diagram in greater detail double demodulator (DL Demodulator) element of the system as shown in FIG. 4 of the signal processing used in the channel separator.

Double demodulator 44 of FIG. 4 is shown in greater detail in FIG. 5, which for clarity also includes electronic driver 20 and probe 10. The received signal $f_{r1}$ from R1 is applied to an RF amplifier 81, and the amplified signal is applied via lead 83 as inputs to multipliers 90 and 92. Similarly, signal $f_{r2}$ from R2 is applied to an RF amplifier 82, and the amplified signal is applied via lead 84 as inputs to multipliers 96 and 98.

The original transmitted carrier frequency $f_0$ is applied as the other inputs to multipliers 90 and 98. The carrier is also phase shifted by 90 degrees by block 85, and the shifted frequency is applied via lead 86 as the other inputs to multipliers 92 and 96.

Multiplier 90 functions to heterodyne $f_{r1}$ and $f_0$ together, producing sum and difference frequencies. These are applied by lead 91 to low pass filter 100, which removes the sum frequency and passed the difference or doppler frequency, $f_{d1}$. Because $f_{r1}$ and $f_0$ are relatively close in frequency, their sum and difference frequencies are far apart, and it is a simple matter to separate them with a low pass filter. In similar fashion, $f_{d2}$ is produced by multiplier 98 and filter 108. Difference components resulting from the phase shifter carrier are produced at leads 103 and 107.

Offset oscillator 94 provides a pilot frequency which is applied to multipliers 112 and 116. A 90 degree phase shifted form of this pilot frequency is applied to multipliers 110 and 118. Multiplier 110 heterodynes the signal from filter 100 and the phase shifted pilot frequency and provides an output on lead 111 which is applied as one input to summer 120. Multiplier 112 heterodynes the signal from filter 102 and the pilot frequency and provides an output on lead 113 which is applied as the other input to summer 120. Multiplier 116 heterodynes the signal from filter 106 and the pilot frequency and provides an output on lead 111 which is applied as one input to summer 122. Multiplier 118 heterodynes the signal from filter 108 and the phase shifted pilot frequency and provides an output on lead 119 which is applied as the other input to summer 122. The output of summer 120 at lead 121 is $f_{d1}$ offset by the pilot frequency, and the output of summer 122 at lead 123 is $f_{d2}$ offset the pilot frequency. These are multiplied in circuit 125, the output low pass filtered at 127, and the resulting signal at lead 36 is $f_{d1}-f_{d2}$.

The above described operation of the double demodulator 44 can further be described as follows:

Driver signal=$\sin2\pi f_o t$

Quadrature signal=$\cos2\pi f_o t$

Receiver R1 signal=$\sin2\pi(f_0+f_{d1})t+\sin2\pi f_0 t$

Receiver R2 signal=$\sin2\pi(f_0+f_{d2})t+\sin2\pi f_0 t$

Offset pilot signal=$\sin2\pi f_p t$

Quadrature offset signal=$\cos2\pi f_p t$

Multiplier 90 output=$\sin2\pi f_0 t[\sin2\pi(f_0\pm f_{d1})t+\sin 2\pi f_0 t]=$ /1;2cos $[2\pi(\mp f_{d1}t)-\cos2\pi(2f_o\pm f_{d1}t)+\frac{1}{2}(1-\cos2\pi(2f_0 t))$ After low pass filter=$\frac{1}{2}\cos2\pi(\mp f_{d1}t)$ After scaling=$\cos2\pi(\mp f_{d1}t)$ Multiplier 92 output=$\cos2\pi f_0 t[\sin2\pi(f_0\pm f_{d1})t+\sin2\pi f_0 t]=$ /1;2[sin $2\pi(2f_0\pm f_{d1})t+sin2\pi(\pm f_{d1}t)]+\frac{1}{2}[\sin2\pi(2f_0 t)]$ After low pass filter=$\frac{1}{2}\sin2\pi(\pm f_{d1}t)$ After scaling=$\sin2\pi(\pm f_{d1}t)$ Multiplier 110 output=$\cos2\pi(f_p t)\cos2\pi(\mp f_{d1}t)$
$=\frac{1}{2}[\cos2\pi(f_p\mp f_{d1})t+\cos2\pi(f_p\pm f_{d1})t]$ Multiplier 112 output=$\sin2\pi(f_p t)\sin2\pi(\pm f_{d1}t)$
$=\frac{1}{2}[\cos2\pi(f_p\mp f_{d1})t-\cos2\pi(f_p\pm f_{d1})t]$ Output of summer 120=$\cos2\pi(f_p\mp f_{d1})t$ By symmetry, output of summer 123=$\cos2\pi(f_p\mp f_{d2})t$ Output of multiplier 125=$\frac{1}{2}[\cos2\pi(2f_p\mp f_{d1}\mp f_{d2})t+\cos2\pi(\mp f_{d1}\pm f_{d2})t]$ Output of low pass filter 127 and with scaling= $\cos2\pi(\pm f_{d1}\mp f_{d2})t$ The channel separator 70 will now be described. Channel separator 70 is used to distinguish between forward and reverse flow frequency components in the received signals. It may happen that the area of tissue being insonated contains both an artery and a vein, and that they have blood flow in opposite directions. This will result in the doppler-shifting of the carrier frequency in both the upward and downward directions, and if a system is not provided for discriminating them, the measurement and calculation process could lead to incorrect results.

The channel separator is shown in detail in FIGS. 6A and 6B. It has two identical signal processing paths, with the components for the signals from R1 having reference numbers with the -a suffix, and those for the signals from R2 having the -b suffix. Multiplier 71a receives and mixes the carrier reference frequency $f_0$ and the received signals $f_{r1}$ from R1. The output consisting of sum and difference signals is sent to FM demodulator 72a. Another FM demodulator 73a receives the signal from summer 120 of FIG. 5, which is $f_{d1}$ offset by the pilot frequency. The outputs of FM demodulators 72a and 73a are applied as inputs to a summer 74a and a subtractor 75a. This provides the forward frequency $f_{f1}$ and reverse frequency $f_{r1}$ at signal points 76a and 77a. The operation of the circuits on the R2 frequency components follows the same pattern as just described, and results in forward frequency $f_{f2}$ and reverse frequency $f_{r2}$ at signal points 76b and 77b. The four signals at 76a, 76b, 77a, 77b are applied to the CPU for use in the blood flow calculations there.

Operation of the channel separator will be seen also from the following:

$f_f$=forward doppler difference frequency $f_r$=reverse doppler difference frequency The driver (carrier reference) voltage=$\sin2\pi(f_0 t)$ The receiver voltage=$\sin2\pi(f_0+f_f)t+\sin2\pi(f_0-f_r)t$ Coherent detection of the above, with scaling:

$$= \sin 2\pi(f_0 t)[(\sin 2\pi(f_0 + f_p)t + \sin 2\pi(f_0 - f_r)t)]$$
$$= \cos 2\pi(2f_0 + f_f)t + \cos 2\pi(2f_0 - f_r)t + \cos 2\pi(f_f t) + \cos 2\pi(-f_r t)$$

After low pass filtering this becomes:
$=\cos2\pi(f_f t)+\cos2\pi(-f_r t)=\cos2\pi(f_f t)+\cos2\pi(f_r t)$ After FM demodulation this becomes:

$= f_f + f_r$ which actually is a voltage proportional to this quantity, $=$ constant $(f_f + f_r)$ The output of the DL demodulator summer 120 (FIG. 5) is $=2\cos2\pi(f_p\mp f_{d1})t=2\cos2\pi(f_p+f_f-f_r)t$ After FM demodulation from $f_p$, the offset pilot frequency (94 in FIG. 5)

$= f_f - f_r$ which actually is a voltage proportional to this quantity, $=$ constant $(f_f - f_r)$ The terms $(f_f+f_r)$ and $(f_f-f_r)$ when applied to the adder and subtractor and division by 2 results in the separation of $f_f$, the forward frequency, and $f_r$, the reverse frequency.

The well-known doppler equation is $$f_d = \frac{f_0}{c} \left[ \frac{\cos A + \cos B}{1 + \frac{v}{c} \cos B} \right]$$

where A is the receiver/blood flow angle, B is the transmit/blood flow angle, c is the speed of sound in tissue, and v is the blood flow velocity. If one of the angles were known, the velocity could be found, but, as pointed out above, the prior art has not been able to do this accurately.

With reference to the geometry of FIG. 3 for the use of the present invention, note that, for R1:

$$f_{d1} = \frac{f_0}{c} \left[ \frac{\cos\theta + \cos(\theta + \alpha)}{1 + \frac{v}{c} \cos(\alpha + \theta)} \right]$$

and for R2:

$$f_{d2} = \frac{f_0}{c} \left[ \frac{\cos(\theta + \alpha + \beta) + \cos(\theta + \alpha)}{1 + \frac{v}{c} \cos(\alpha + \theta)} \right]$$

Taking the ratio:

$$\frac{f_{d2}}{f_{d1}} = \frac{\cos(\theta + \alpha) + \cos(\theta + \alpha + \beta)}{\cos(\theta + \alpha) + \cos\theta} \equiv k$$

Solving for θ:

$$\theta = \tan^{-1}\left[\frac{(\cos\alpha)\left(1-\frac{1}{k}\right)-\frac{1}{k}\cos(\alpha+\beta)}{(\sin\alpha)\left(1-\frac{1}{k}\right)-\frac{1}{k}\sin(\alpha+\beta)}\right]$$

Therefore, if the ratio k can be determined, then the angle θ can be calculated, and the velocity v can then be determined. A problem in taking the ratio k directly from measurements of $f_{d1}$ and $f_{d2}$ is that these quantities are not discrete frequencies but are spectra of ranges of frequencies, resulting from the fact that reflections will be received from red blood cells in moving at different speeds in different parts of the vessel. In prior art systems, various estimates or spectral analysis steps have been performed at this point, with varying degrees of success, usually involving some approximations. In the present system, when $f_{r1}-f_{r2}$ is determined, it is developed in hardware using instantaneously varying frequencies, so there is no need for analyzing or filtering the spectrum of frequencies.

In the operation the various signals developed in the systems of FIGS. 4, 5, and 6 are provided to the CPU, in digitized form. They are stored in memory over a number of pulse cycles, and also processed and displayed in real time.

The raw signals from one of the receivers may be detected, low pass filtered, amplified, and played over an audio speaker mounted in electronics 13. When blood flow is being insonated, the doppler components in the audio range produce a "whoosh" noise. This does not provide any significant quantitative information, but is useful to the operator in placing the probe. The signals from R1 and R2 are also passed through a threshold detector, and displayed on the CRT screen of the computer as a pair of bar graphs, seen in FIG. 1. This is useful in making sure there is reliable data being received by both detectors before measurements are taken. For example, if the probe were leaned over far enough to cause one receiver to come out of contact with the skin, its signal would fall below threshold, and its weak output would also show on the bar graph, to tell the operator.

Assuming good signal strength, the CPU selects one of the forward or reverse received components, preferably the one with the highest absolute value frequency shift. This will be the artery which has higher velocity than the vein, and will be from the receiver closest to parallel to the artery. This can be an automatic selection based on this criterion, or a manual selection can be made by operator input to the computer. For the selected received value, the system measures the bandwidth, and sets $f_{r1}$ to the upper 3db point of this bandwidth. Other references could also be used, but at present this one has proved satisfactory. Using this value of $f_{r1}$, the system solves for $f_{r2}$. Then ratio K is then calculated, which permits solving for θ, and the velocity, in cm per second, using the above equations.

This can be updated constantly and displayed on the CRT. Also, the calculated velocity signal can also be displayed on the CRT as a scrolling waveform with velocity on the vertical axis and time on the horizontal axis. This appears as a rough periodic signal at the heartbeat rate, with the waveform being made up of vertical lines corresponding to the spectra of received velocities.

Because the displayed velocity numbers change, and the velocity waveform scrolls so fast, it is desirable to store an interval of time in the computer memory, then recall and display it slowly for study. Using known computer interface techniques, in a memory mode the operator can move a cursor along the stored waveform, and the calculation and display of the velocity repeatedly for that chosen time slice.

Another feature is peak velocity/frequency detection. In order to measure peak velocity, it is necessary to analyze the two doppler difference return signals and determine the peak frequency of each, regardless of amplitude (excepting noise). This necessitates a peak frequency follower or detector. Most prior art systems measure peak velocity by performing Fourier transforms of the audio signal, in software, hardware or firmware. This has been difficult, given the speed limitations of many computers and the time varying nature of the doppler signal, along with the finite time needed to perform a Fourier transform.

Figure 7:
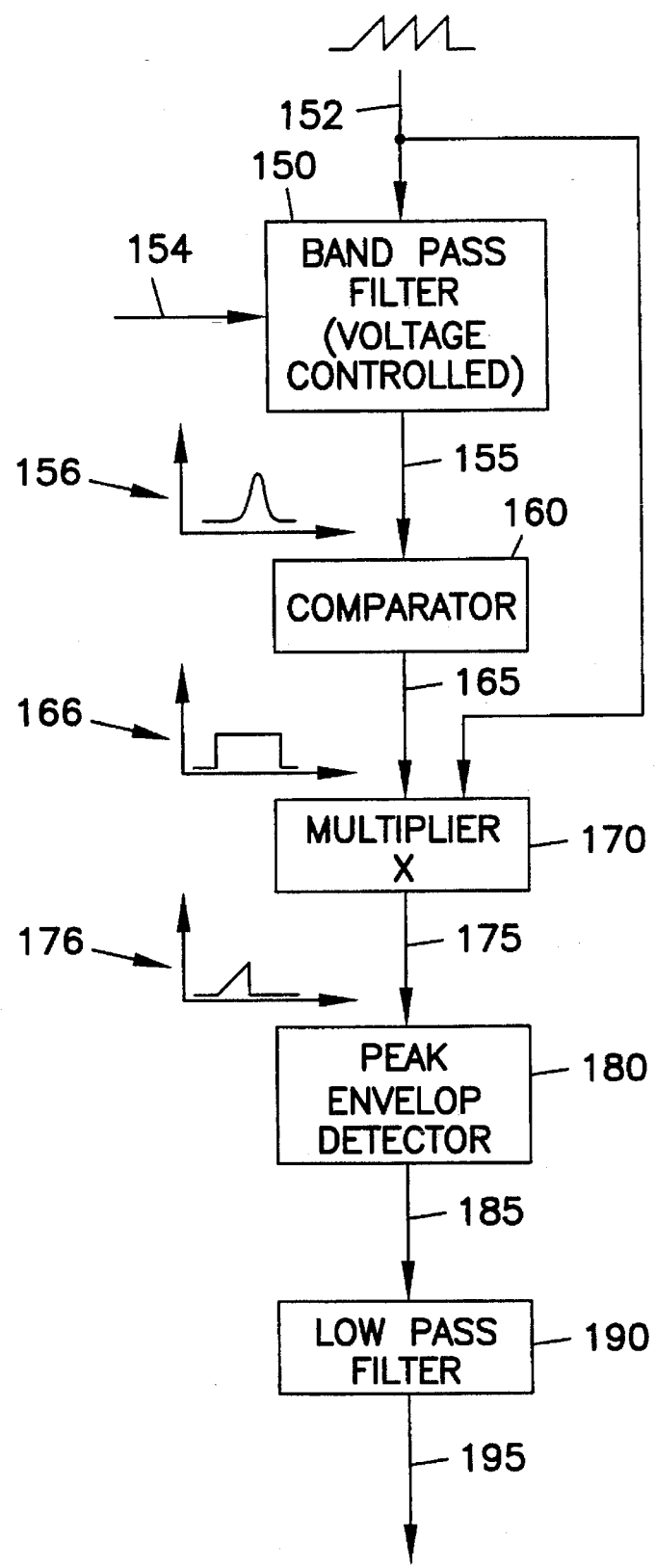
FIG. 7 is a block diagram illustrating the operation of the peak flow velocity measurement feature.

The present invention provides a time domain peak frequency measurement to overcome these limitations. In FIG. 7 a voltage controlled bandpass filter 150 receives a sawtooth waveform on lead 152, and the doppler signal on lead 154. The filter sweeps its bandpass in response to the sawtooth. For example, the filter may sweep from 0 to 10 KHz repeatedly, with the Q of the filter being high and the passband narrow, for example 10 Hz. The sweep rate is much higher than the pulse rate of the patient, so that the filter can capture the doppler signal's time variations. The output of the filter is fed over lead 155 to a comparator 160 which functions to chop and square the signals to thereby equalize the amplitude components of the contributing frequencies. This chopped signal is then multiplied with the sawtooth in multiplier 170 to result in a chopped sawtooth. The highest amplitude (in the time domain) will now indicate the highest frequency (in the frequency domain). This information on lead 173 may be fed into a computer for analysis to recover the highest frequency. Alternatively, as indicated in FIG. 7, it may be passed through a peak envelope detector 180 and low pass filter 190. The output at 195 will be a time domain signal proportional to peak frequency. This can be fed into the computer, and stored and displayed.

The overall operation of all of the steps and subsystems of the invention, which have been individually described above, will now be explained with reference to the flow diagram FIG. 8. Step 200 is the process of placing the probe on the skin, transmitting the ultrasonic energy, and receiving the return signals reflected from the blood. Step 210 represents the signal processing steps of (1) determining the ratio K, (2) separating the forward and reverse channels, and (3) determining peak velocity, each of which processes has been described above in detail. Since these steps can be performed in different orders, including somewhat interdependently, they have been included as one step 210. The various signals developed are passed on for digital processing. Also, the audio output of the doppler frequency can by output at step 212.

Figure 8:
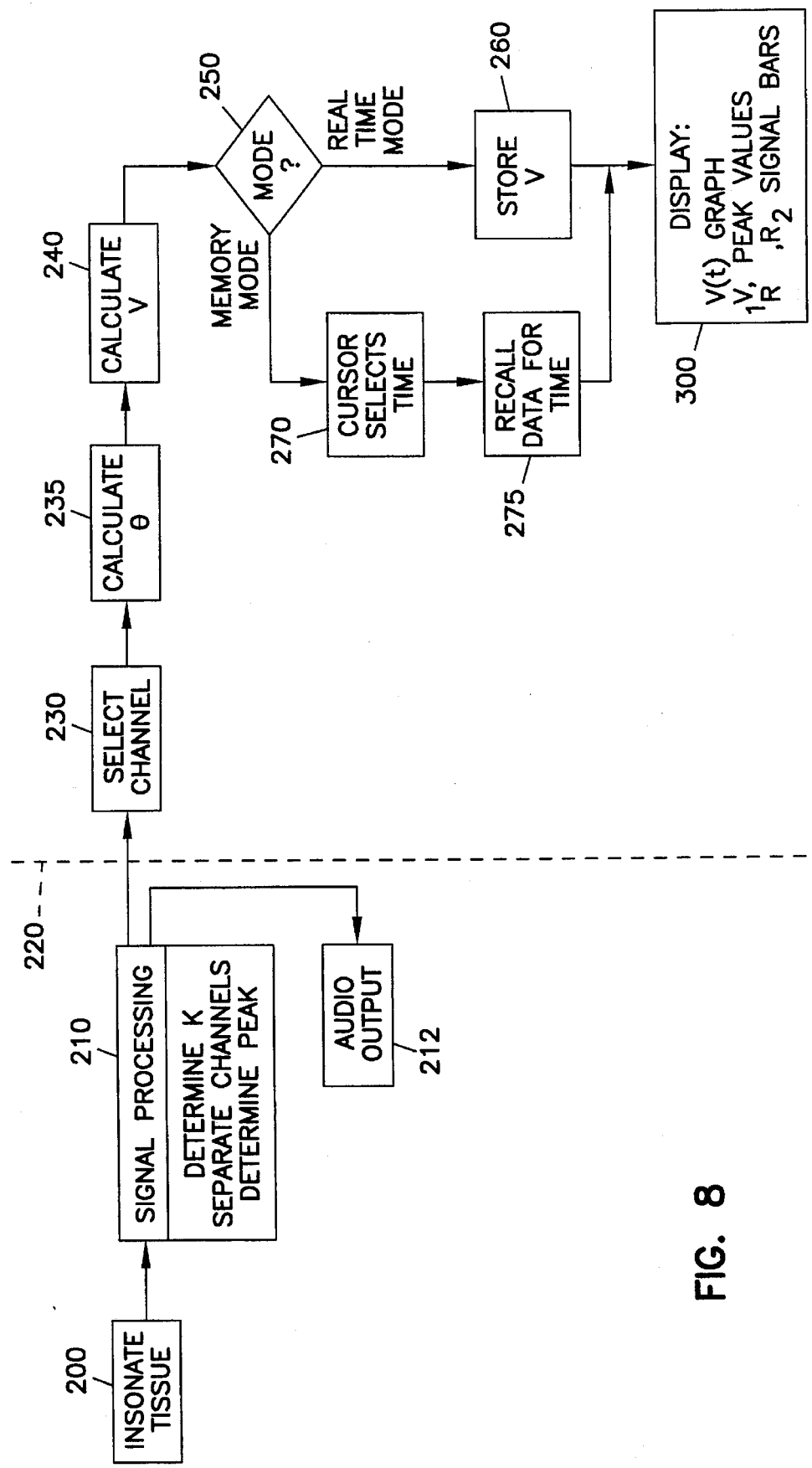
FIG. 8 is a schematic diagram illustrating the operation of the invention.

In FIG. 8, dashed line 220 represents the transition from analog processing to digital processing in the presently preferred embodiment. As previously explained, this location for the transition is chosen out of consideration of a balance of speed and cost factors, but more or less of the processing steps can be done in analog or digital, as desired.

The channel to be measured is selected at step 230. As mentioned, this is preferably the larger doppler signal, representing a artery, as measured by the receiver which is closer to parallel to the flow. The angle θ is calculated at step 235, and from this the correct velocity can be calculated at step 240.

The next step depends on the mode of operation which has been selected by the operator, through appropriate input commands to the computer. In the real time mode, control passes through 250 to step 260, where calculated data is stored in the computer memory. Typically from several seconds to several minutes worth of data could be stored, for analysis later. Alternatively, unprocessed data could be stored, and calculated at such later time as it is needed. The current data is also displayed on the computer display at step 300. This operation is repeated continuously at a high data rate, to give real time measurement and display. However, because this will result in the velocity numbers on the display changing too fast to read or interpret, it may be necessary to use a memory mode for studying the results of measurement.

In a memory mode of operation, the display is made to operate on previously stored data. In this mode, the operator selects data for a previously stored interval of time, as represented at step 270. This selection can be done by any known technique, for example by using the computer mouse or other pointing device to position the cursor on the portion of the displayed pulse waveform of interest. At step 275, the data for the desired interval is recalled from memory and displayed. This is updated so that any desired time may be viewed.

At step 300, the results of measurement are displayed, either the real time values or previously stored values. This preferably includes a display of a number of items as seen in FIG. 1. This includes the signal bar graphs of the two receivers, the pulse-like scrolling waveform of the received signals or spectra, and numeric displays of the measured velocity of the blood flow, and/or the peak velocity.

In operation, the probe angle independence of the measurement can be verified by moving the probe through an angle, and noting that the values to not change, until such movement essentially takes the focus out of the flow.

It will be seen from the above that the present invention provides an improved ultrasonic blood flow velocity measurement, which is reliable, repeatable, and which gives accurate measurements of velocity, independently of probe angle and the presence of venous and arterial flow in the same area of tissue.

I claim:

1. A method of measuring blood flow velocity within a vessel, comprising the steps of:
    a) insonating tissue containing the vessel along a path of transmitted continuous wave ultrasonic energy;
    b) receiving an ultrasonic energy signal containing doppler shifted frequencies, the ultrasonic energy signal reflected from the blood flow, along two paths which are at known angles to the path of transmitted ultrasonic energy;
    c) determining the ratio of the doppler shifted frequencies of the ultrasonic energy signal reflected from the blood flow along the two paths;
    d) calculating the angle between at least one of the paths of ultrasonic energy and the direction of blood flow based upon the ratio;
    e) determining the velocity of the blood flow based upon the doppler shifted frequencies and the calculated angle; and
    f) displaying the blood flow velocity.

2. The method of claim 1, wherein the ratio is taken between one of the doppler shifted frequencies as an instantaneous time varying frequency, and a relatively slow-varying fixed point on the measured bandwidth of the other doppler shifted frequencies.

3. The method of claim 1, further including the step of measuring peak flow velocity by time domain processing of the received ultrasonic energy signals.

4. The method of claim 3, wherein the time-domain processing of the received ultrasonic signal comprises the steps of:

bandpass filtering the received ultrasonic signal to produce a filtered received signal;

generating a variable duration comparator output pulse by comparing the filtered received signal to a reference signal;

forming a variable peak sawtooth signal by multiplying the variable duration comparator output pulse by a sawtooth waveform; and forming a peak envelope signal by detecting peaks of the variable peak sawtooth signal.

5. The method of claim 4, further comprising low pass filtering the peak envelope signal.

6. The method of claim 4, wherein the step of bandpass filtering the received ultrasonic signal uses a triggered swept passband and a swept frequencies bandwidth through which the passband is swept.

7. The method of claim 6, wherein a bandwidth of the passband is much smaller than the swept frequencies bandwidth.

8. The method of claim 7, wherein a trigger rate at which the passband is swept through the swept frequencies bandwidth is much higher than time variations in the received ultrasonic signal.

9. The method of claim 1 further including the steps of:
    measuring forward and reverse frequency shifts of the doppler shifted frequencies for the received ultrasonic energy signals along the two paths; and
    determining from the measured forward and reverse frequency shifts where there are opposite blood flows in vessels in the insonated area.

10. The method of claim 9, wherein the step of measuring forward and reverse frequency shifts for the received ultrasonic energy signal along at least one of the two paths comprises:
    forming a first signal proportional to the sum of the forward frequency shift and the reverse frequency shift;
    forming a second signal proportional to the difference between the forward frequency shift and the reverse frequency shift;
    adding the first signal and the second signal to obtain a signal proportional to the forward frequency shift;
    subtracting the second signal from the first signal to obtain a signal proportional to the reverse frequency shift; and
    thereby measuring the forward and reverse frequency shifted signals.

11. The method of claim 10, wherein the step of adding the first signal and the second signal further comprises scaling a resulting signal.

12. The method of claim 10, wherein the step of subtracting the second signal from the first signal further comprises scaling the resulting signal.

13. The method of claim 10, wherein the step of forming a first signal proportional to the sum of the forward frequency shift and the reverse frequency shift comprises multiplying the received ultrasonic energy signal by a carrier signal of frequency substantially the same as the frequency of the transmitted continuous wave ultrasonic energy to form a mixed signal and demodulating the mixed signal.

14. The method of claim 13, wherein the step of demodulating the mixed signal comprises the step of low-pass filtering the mixed signal.

15. The method of claim 10, wherein the step of forming a second signal proportional to the difference between the forward frequency shift and the reverse frequency shift comprises:

forming an unshifted carrier-mixed signal;

forming a shifted carrier-mixed signal;

multiplying the unshifted carrier-mixed signal by a shifted pilot signal to form a first carrier-pilot mixed signal;

multiplying the shifted carrier-mixed signal by an unshifted pilot signal to form a second carrier-pilot mixed signal;

summing the first carrier-pilot mixed signal and the second carrier-pilot mixed signal to form a summed carrier-pilot mixed signal; and demodulating the summed carrier-pilot mixed signal.

16. The method of claim 15, wherein the summed carrier-pilot mixed signal has a frequency that is substantially the same as the sum of the frequency of the pilot signal and the difference between the doppler shifted frequency of the received ultrasonic energy signal and the frequency of the transmitted continuous wave ultrasonic energy.

17. The method of claim 15, wherein the shifted pilot signal and the unshifted pilot signal are approximately 90 degrees out of phase.

18. The method of claim 15, wherein the step of forming an unshifted carrier-mixed signal comprises multiplying a signal proportional to the received ultrasonic energy signal by the carrier signal and low-pass filtering a resulting first product signal.

19. The method of claim 15, wherein the step of forming a shifted carrier-mixed signal comprises multiplying a signal proportional to the received ultrasonic energy signal by a shifted carrier signal which is approximately 90 degrees out of phase with the carrier signal, and low-pass filtering a resulting second product signal.

* * * * *